(12) United States Patent
Sampson et al.

(10) Patent No.: US 10,428,100 B2
(45) Date of Patent: Oct. 1, 2019

(54) SUBSTITUTED LEAD HALIDE PEROVSKITE INTERMEDIATE BAND ABSORBERS

(71) Applicant: UCHICAGO ARGONNE, LLC, Chicago, IL (US)

(72) Inventors: Matthew D. Sampson, Oak Park, IL (US); Maria K. Chan, Burr Ridge, IL (US); Alex B. Martinson, Naperville, IL (US)

(73) Assignee: UChicago Argonne, LLC, Chicago, IL (US)

( * ) Notice: Subject to any disclaimer, the term of this patent is extended or adjusted under 35 U.S.C. 154(b) by 332 days.

(21) Appl. No.: 15/406,419

(22) Filed: Jan. 13, 2017

(65) Prior Publication Data

US 2018/0201637 A1 Jul. 19, 2018

(51) Int. Cl.
  *C03C 8/00* (2006.01)
  *C07F 15/06* (2006.01)
  *C07F 7/24* (2006.01)
  *H01L 51/00* (2006.01)
  *H01G 9/20* (2006.01)

(52) U.S. Cl.
  CPC .............. *C07F 15/065* (2013.01); *C07F 7/24* (2013.01); *H01L 51/005* (2013.01); *H01G 9/2045* (2013.01)

(58) Field of Classification Search
  USPC .................................................. 428/426, 688
  See application file for complete search history.

(56) References Cited

U.S. PATENT DOCUMENTS

| | | |
|---|---|---|
| 6,444,897 B1 | 9/2002 | Luque-Lopez et al. |
| 7,414,294 B2 | 8/2008 | Forrest |
| 7,750,425 B2 | 7/2010 | Forrest et al. |
| 8,232,470 B2 | 7/2012 | Walukiewicz et al. |
| 9,240,507 B2 | 1/2016 | Yoshikawa et al. |
| 2016/0149145 A1 | 5/2016 | Mhaisalkar et al. |

OTHER PUBLICATIONS

Sampson, M.D., et al., "Substituted Lead Halide Perovskite Intermediate Band Absorbers," Materials Science Division, Argonne, Illinois, 2016, pp. 1-10.
Sogabe, T., et al., "Intermediate-band dynamics of quantum dots solar cell in concentrator photovoltaic modules," Scientific Reports, 4: 4792, Apr. 25, 2014, pp. 1-7.

*Primary Examiner* — Lauren R Colgan
(74) *Attorney, Agent, or Firm* — Foley & Lardner LLP

(57) ABSTRACT

Lead halide perovskites have proven to be a versatile class of visible light absorbers that allow rapid access to the long minority carrier lifetimes and diffusion lengths desirable for traditional single-junction photovoltaics. Computational screening identified both Fe- and Co-substituted $MAPbBr_3$ as promising intermediate band candidate materials, and the later films were synthesized via conventional solution-based processing techniques. First-principles density functional theory (DFT) calculations support the existence of intermediate bands upon Co incorporation and enhanced sub-gap absorption, which are confirmed by UV-visible-NIR absorption spectroscopy. The simple tenability combined with steady state and time-resolved PL studies that reveal no sign of self-quenching suggest this class of materials to be promising for intermediate band photovoltaics.

20 Claims, 14 Drawing Sheets

(b)

(c)

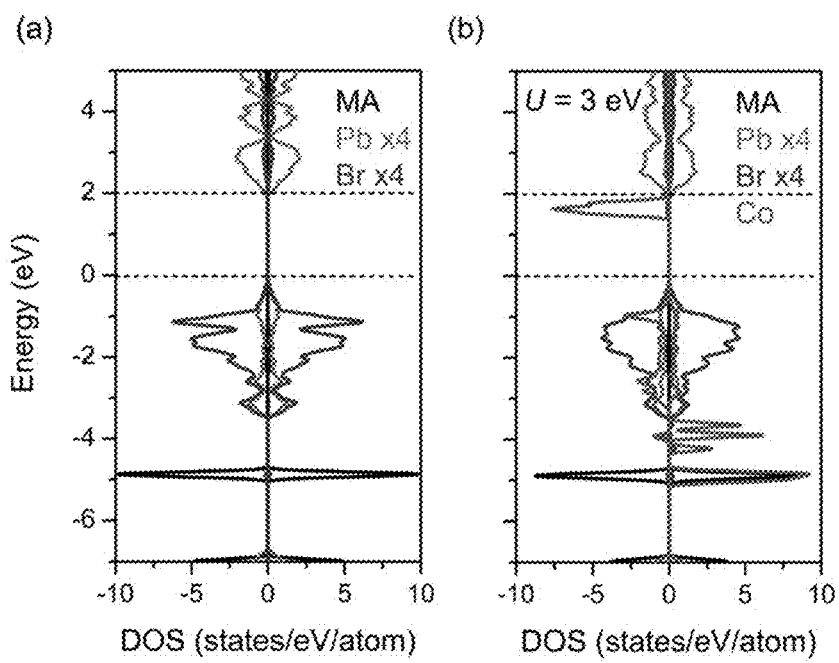
Figure 5A
Figure 5B
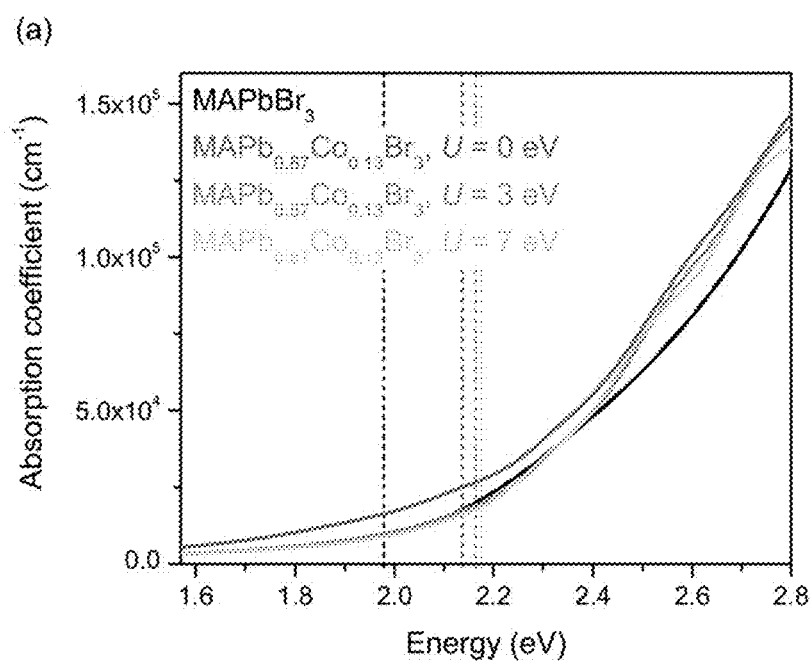
Figure 6A

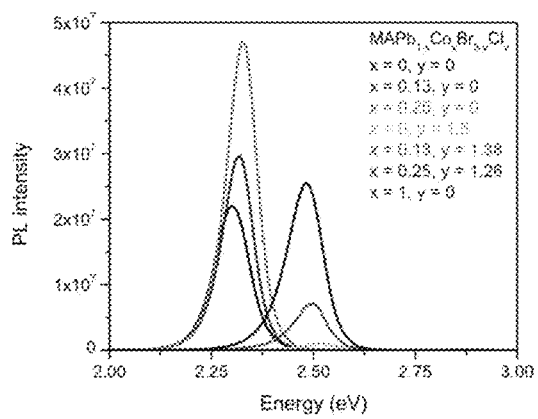
Figure 26
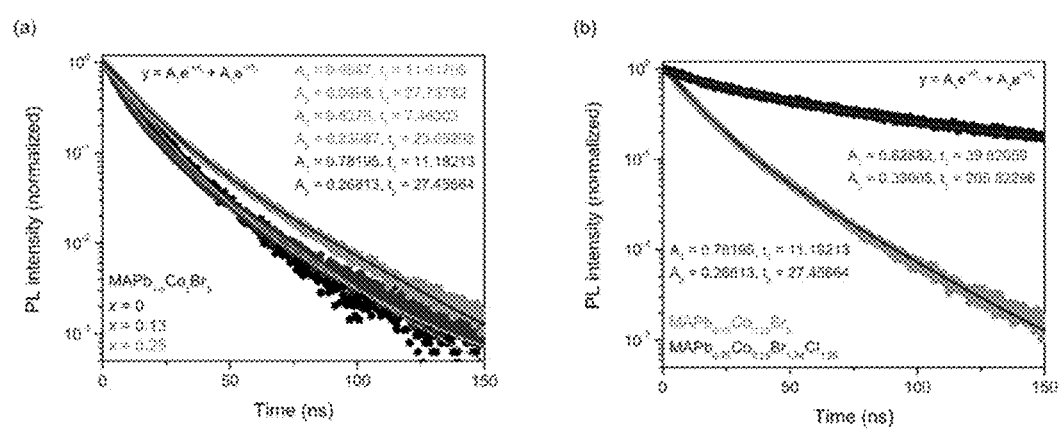
Figures 27A-B Exponential fits for the time-resolved PL data shown in Figure 4.

SUBSTITUTED LEAD HALIDE PEROVSKITE INTERMEDIATE BAND ABSORBERS

The United States Government claims certain rights in this invention pursuant to Contract No. W-31-109-ENG-38 between the United States Government and the University of Chicago and/or pursuant to DE-AC02-06CH11357 between the United States Government and UChicago Argonne, LLC representing Argonne National Laboratory.

TECHNICAL FIELD

The present disclosure relates generally to perovskites and methods of forming same.

BACKGROUND

Lead halide perovskite semiconductors have been extensively studied for a variety of optoelectronic applications, including photovoltaics (PVs), photodetectors, and LEDs. There has been considerable interest in these materials due to their tunable optical properties, large absorption coefficients, excellent mobilities, long excited state lifetimes, low cost, and simple solution-based deposition techniques by which most are commonly formed. Since the first report of these materials as light absorbers in single-junction photovoltaics in 2009, power conversion efficiencies exceeding 20% have been realized and rationalized owing to their excellent photophysical properties.

Intermediate band (IB) PVs are a class of multi-junction devices that have the theoretical ability to surpass the Shockley-Quessier of single p-n junction cells. IB PVs require an IB material sandwiched between two conventional (n- and p-type) semiconductors, which serve as selective contacts to the conduction band (CB) and valence band (VB), respectively. These PVs are designed to retain the high output voltages characteristic of large band gap semiconductors while harvesting significantly more of the available solar spectrum by absorbing pairs of sub-band gap photons to produce additional high-energy carriers. Only a handful of examples of materials that exhibit the properties necessary for IB PV operation have been reported to date. GaAs is the most successful parent material to date owing to its excellent photophysical properties, to which perovskite halides have been compared, as well as the ability to form quantum wells with smaller gap. While the GaAs-quantum wells operate as IB PVs, the sub-parent-bandgap contribution to the photocurrent is meager as it is limited by the achievable density of the structurally strained quantum wells. The bandgap of GaAs is also not ideal, as the optimal total band gap of an IB material has been calculated to be approximately 2.0 eV, which is split by a mid-gap level into two sub-band gaps of approximately 0.7 eV and 1.3 eV (FIG. 1). In this arrangement, the maximum photovoltage is the difference between the quasi-Fermi levels (i.e. the electrochemical potentials of the electrons) in the CB and VB of the n- and p-side electrodes (2.0 eV).

Lead halide perovskites may be prime candidates for this application due to their outstanding photophysical properties, suspected structural tolerance for metal substitution, and tunable band gap. Compared to conventional inorganic binary semiconductors like GaAs (band gap=1.4 eV), a large compositional space has been identified for $APbX_3$ perovskites (A=cations such as $Cs^+$, methyl ammonium [MA], or formamidinium [FA] and X=Cl, Br, and/or I). While some elements have been substituted for Pb in the $APbX_3$ perovskite structure, those have been in the same group IV, Sn and Ge, as well as related (periodic table near neighbors) Bi and Hg. These alternatives have garnered interest as a compromise in order to avoid the toxicity of Pb but at the expense of stabilities and device performances as compared to their Pb-containing analogues. Recently, Bi has also been utilized in conjunction with Ag to form the double perovskite $Cs_2Ag^IBi^{III}Br_6$, which exhibits an encouraging photoluminescence lifetime, but only a single gap, and only in single crystal form.

SUMMARY

Embodiments described herein relate generally to A substituted perovskite comprising a material having the formula: $APb_{1-x}B_xBr_{3-y}Cl_y$, where A is a cation, B is Fe or Co, X is greater than 0 and less than 1 and y is 0-3).

Other embodiments relate to a substituted perovskite comprising a material having the formula: $MAPb_{1-x}B_xBr_{3-y}H_y$, where MA is methyl ammonium, B is Fe or Co, H is a halide, X is 0 to 0.5 and y is greater than 0 and less than 3.

Yet other embodiments relate to an article of manufacture comprising a glass substrate. The article of manufacture further comprises a material deposited on the glass substrate having the formula: $APb_{1-x}B_xBr_{3-y}Cl_y$, where MA is methyl ammonium, B is Fe or Co, X is 0 to 1 and y is 0 to 3.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIGS. 5A-B. Calculated electronic structure of (a) $MAPbBr_3$ and (b) $MAPb_{0.87}Co_{0.13}Br_3$. In the density functional theory (DFT) calculations, a Hubbard U of 3 eV is used for Co d orbitals. The dashed horizontal lines represent the band edges of pure $MAPbBr_3$ estimated by the N 2s semicore level as reference in the calculations. The density of states of the Co-substituted system is broader than that of the pure system.

FIGS. 6A-B. (a) Calculated absorption coefficient of $MAPb_{0.87}Co_{0.13}Br_3$ with U values (for Co 3d orbitals) of 0 (red), 3 (orange), and 7 eV (yellow) as compared to the calculated absorption coefficient of $MAPbBr_3$ (black). The calculated band gaps are indicated with vertical dotted lines. (b) Change in absorption coefficient ($\Delta\alpha$) of $MAPb_{0.87}Co_{0.13}Br_3$ from $MAPbBr_3$ for experimental (black) and computations (red, U=3 eV).

FIG. 26. Non-normalized steady state PL spectra of $MAPb_{1-x}Co_xBr_{3-y}Cl_y$ thin films. The spectrum of a control film consisting of a 1:1 ratio of $CoBr_2$ to MABr is shown.

FIGS. 27A-B. Exponential fits for the time-resolved PL data shown in FIG. 4.

Figures 1A, 1B:
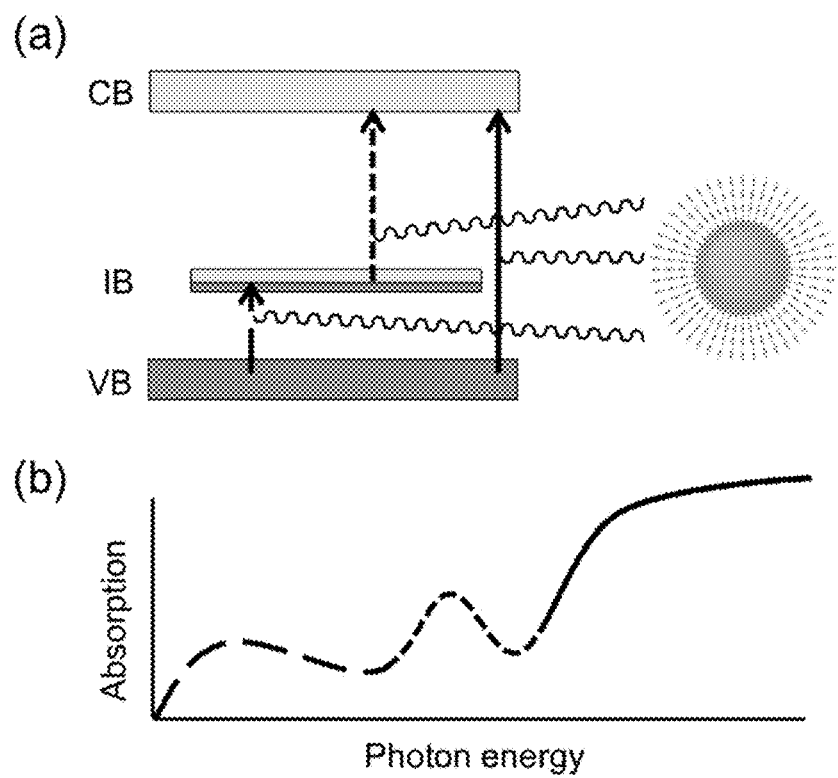
FIGS. 1A-B. (a) Schematic displaying the working principle of an IB PV. (b) Corresponding absorption spectrum of the idealized IB PV.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to thin film fabrication of a substituted perovskite. Applicants have identified MAPb(Br or Cl)$_3$ as a promising parent material with nearly ideal parent band gap (~2.2 eV) to prior perovskites and hypothesize that partial substitution of Pb for earth-abundant transition metals could provide stable mid-gap states with tunable energy level, while retaining most of the desirable optoelectronic attributes of the parent material. Some embodiments relate to $APb_{1-x}B_xBr_{3-y}Cl_y$, A is a cation, B is a transition metal, x is 0 to 1, and y is 0-3) and the methods of forming same.

To that end, computational high throughput screening with density functional theory (DFT) was used to identify Pb-site substituents in the MAPbX$_3$ (were MA is methyl ammonium, and X is Cl, Br or I) perovskite framework that would result in a sub-band gap density of states capable of fulfilling IB requirements. From this screening, Fe and Co were selected among over 60 elements for experimental synthesis and investigation. DFT calculations predicted minimal structural changes and near-zero thermodynamic penalty with ⅛ Fe or Co substitutions on the Pb site, indicating the possibility of Fe and Co incorporation into the structural framework. Electronic structure calculations predicted that substitution should produce Fe- or Co-based sub-band gap states capable of functioning as IBs.

The screening was set to provide embodiments that will create an intermediate band near the optimal energy within the gap (1.3 eV from VB maximum [VBM] or −0.7 eV from CB minimum [CBM]). DFT screening of over 60 elements for Pb-site substitution in the MAPbBr$_3$ cubic perovskite structure revealed that both Fe and Co, among others, should produce a discrete density of states within the parent gap.

Following computational study of Fe- and Co-substituted materials, MAPb$_{1-x}$Co$_x$Br$_{3-y}$Cl$_y$ thin films were synthesized and characterized as further described below. These thin films were characterized by XRD, UV-Vis-NIR absorption spectroscopy, and PL spectroscopy to understand the effect of Fe and Co substitution on the structural and photophysical properties of the perovskite films. XRD and elemental measurements proved that Fe and Co were incorporated into the perovskite framework, resulting in minimal change to film crystallinity. UV-Vis-NIR spectroscopy revealed a sub-band gap absorption features for Co-substituted samples; however, Fe substitution did not reveal sub-gap absorption. Steady state and time-resolved PL revealed that Co substitution does not quench PL, which suggests this class of materials may be promising for IB PVs. Further investigation of the Co-induced density of states in these materials by time-resolved spectroscopies and device fabrication will reveal the true potential of this exciting material.

In particular, certain embodiments are related to thin films of Fe- and Co-substituted, i.e. MAPb$_{1-x}$B$_x$Br$_{3-y}$Cl$_y$ (where B is Fe or Co, x is 0 to 1, greater than 0 to 1, 0 to 0.5, greater than 0 to 0.5, 0.13 to 1, 0.13 to 0.5, 0.25 to 1.0, 0.25 to 0.5 and where y is 0 to 3, greater than 0 to 3, 0 to 1.25, greater than 0 to 1.25, 1.5 to 3, 1.5 to 3, 1.25 to 1.5). In one embodiment, the $^{-1}$ anion is a halide. Here, Applicant reports the synthesis and characterization of Fe- and Co-substituted MAPbBr$_{3-y}$Cl$_y$ (i.e. MAPb$_{1-x}$Fe$_x$Br$_{3-y}$Cl$_y$ and MAPb$_{1-x}$Co$_x$Br$_{3-y}$Cl$_y$) thin films, prepared via one-step solution-processing. Methods as reported previously in the art can b used to spin coat a solution, where the M (such as cobalt) is added into the spin coating solution. The thin films may be prepared by a one-step solution spin coating, following a method adapted from previous reports, such as, for example, as described in Park, B.-W.; Philippe, B.; Zhang, X.; Rensmo, H.; Boschloo, G.; Johansson, E. M. J. Bismuth Based Hybrid Perovskites A$_3$Bi$_2$I$_9$(A: Methylammonium or Cesium) for Solar Cell Application. *Adv. Mater.* 2015, 27, 6806-6813, incorporated herein by reference. In each case, the appropriate ratio of 0.25 M MABr/MACl, PbBr$_2$/PbCl$_2$, and FeBr$_2$/CoBr$_2$ is heated in dimethylformamide (DMF) at 100° C. for 4 hrs. The "appropriate" amount/concentration could be a wide range of values as would be appreciated by one skilled in the art. The concentration is believed to likely affect film thickness. For some embodiments, a concentration of 0.25 M was picked due to solubility, with such being on the high end for solubility for the CoBr$_2$ precursor. In other embodiments, the concentration may be ~0-2 M if the solubility allows for it. For some embodiments for starting materials, a Pb$^{2+}$ salt, halide (Cl, Br, I) source, or a Co$^{2+}$/Fe$^{2+}$ salt may be used. The temperature range for the heating step, in some embodiments, is 90° C. to 150° C. and the time for the heating is an amount sufficient to fully solubilize/homogenize the precursors. In one embodiment, a time in excess may be chosen to ensure full solubization, such as 4 hours, but it is believed that 20 minutes will be sufficient for some embodiments. An excess of MABr/MACl was added to each solution to ensure all PbBr$_2$/PbCl$_2$ was converted to perovskite. In one embodiment, the amount added is sufficient to drive the conversion to completion, such as an approximate 3%

The appropriate substrate, for example any glass substrate. In specific embodiments, fused quartz [FQ] is used for its transparency for optical characterization or fluorine-doped tin oxide [FTO] for it device manufacturing, are selected. In one embodiment, the substrate is pre-cleaned, such as with a 10 min UV/ozone treatment. The substrate is then heated at 90° C. to 150° C., for example 100° C. for 30 min, before spin coating. Immediately before spin coating, the precursor solution was filtered and dropped onto the substrate. Films were spun at 500 rpm-5000+ rpm, for a minimum of 30 seconds, for example 2000 rpm for 30 sec, followed by immediate annealing at 75-150° C. for 10 or more minutes, for example at 100° C. for 30 min. Spin speed is believed to affect film thickness. The temperature and the time are selected to ensure full crystallization. In one method, films can be stored in a dry, inert environment, such as a dry, nitrogen-filled glovebox until further use. In one embodiment, the resulting films are between 200-300 nm thick by optical profilometry (sample thicknesses as measured using an Ambios Technology XP-1 stylus profilometer).

Thin films are characterized by X-ray diffraction (XRD), UV-Vis absorption spectroscopy, and photoluminescence (PL) spectroscopy to understand both the structural and photophysical dependences on the substitution level (x). DFT calculations predict minimal structural changes and near-zero thermodynamic penalty with ⅛ Fe or Co substitutions on the Pb site, indicating the possibility of Fe and Co incorporation into the structural framework and corroborating XRD measurements. Electronic structure calculations further show Fe- and Co-induced deep levels in the band gap and sub-gap absorption, consistent with UV-Vis results for the Co-substituted sample. Although predicted by computations, substitution with Fe did not produce a sub-gap absorption. Finally, time-resolved photoluminescence reveals the potential for these materials in future IB PV.

Thin Film Fabrication. Thin films of Fe- and Co-substituted MAPbBr$_{3-y}$Cl$_y$ (MAPb$_{1-x}$Fe$_x$Br$_{3-y}$Cl$_y$ and MAPb$_{1-x}$Co$_x$Br$_{3-y}$Cl$_y$, Co samples (Figure) were prepared on either fused quartz (FQ) or fluorine-doped tin oxide (FTO) by simple one-step spin coating, following a method adapted from previous reports (see Jeng, J.-Y.; Chiang, Y.-F.; Lee, M.-H.; Peng, S.-R.; Guo, T.-F.; Chen, P.; Wen, T.-C. CH3NH3PbI3 Perovskite/Fullerene Planar-Heterojunction Hybrid Solar Cells. *Adv. Mater.* 2013, 25, 3727-3732.) Dimethylformamide (DMF) solutions of the appropriate precursors (PbBr$_2$, PbCl$_2$, MABr, MACl, FeBr$_2$, and/or CoBr$_2$) were spun onto a pre-heated substrate at 2000 rpm for 30 sec and annealed at 100° C. Attempts to prepare Fe- or Co-substituted perovskite films via two-step deposition or adding solvents or other additives to single-step deposition did not result in any observable improvements in film morphology or grain size as compared to one-step deposition. Attempts were made to soak MAPbBr$_{1-y}$Cl$_y$ films in FeBr$_2$ or CoBr$_2$ solutions in isopropanol; however, in most cases, this resulted in destruction of the films.

Initially, Fe- and Co-substituted films were only prepared by substituting the bromide-only parent material, MAPbBr$_3$. Cl was later introduced in order to better support Fe2+ and Co2+ ions in the perovskite framework, as Cl is expected to give a more stable perovskite 'tolerance factor' and 'octahedral factor'. The Goldschmidt tolerance factor (t) for an ABX$_3$ perovskite is calculated as $$t=(rA+rX)/(2^{1/2}[rB+rX]),$$

where rA, rB, and rX are the ionic radii for the cation (A), metal (B), and halide (X) sites, respectively. The 'octahedral factor' (μ) is simply the ratio of the ionic radius of B and X atoms, and is calculated as follows:

$$\mu=rB/rX$$

Together, the tolerance factor and octahedral factor have been established as widely accepted metrics for determining perovskite halide stability. Perovskite halides possess tolerance and octahedral factors in the ranges of 0.813-1.107 and 0.442-0.895, respectively. In qualitative terms, as Fe2+ (rFe=92 pm) and Co2+(rCo=90 pm) have a much smaller ionic radii than Pb2+(rPb=129 pm), one would expect smaller Cl— (rCl=181 pm) to better support Fe2+ and Co2+ in the perovskite structure as compared to Br— (rBr=196 pm). For Fe2+, t=0.923 and 0.935 and μ=0.469 and 0.508 for Br— and Cl—, respectively. For Co2+, t=0.930 and 0.942 and μ=0.459 and 0.497 for Br— and Cl—, respectively. For both Fe2+ and Co2+, the octahedral factor for Br— yields a μ on the border of predicted stability for perovskite halides.

Figure 9A:
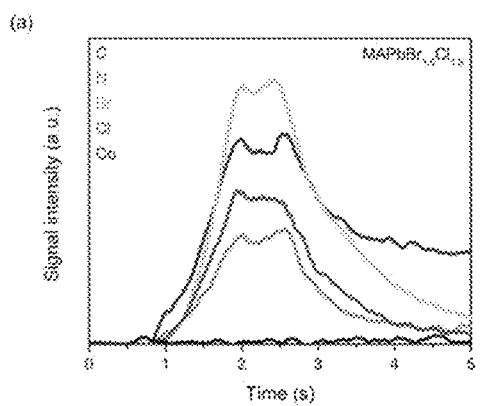
FIGS. 9A-B. Glow discharge optical emission spectroscopy (GDOES) of FIG. 9A $MAPbBr_{1.5}Cl_{1.5}$ and FIG. 9B $MAPb_{0.75}Co_{0.25}Br_{1.75}Cl_{1.25}$ thin films. The signals for oxygen and hydrogen have been omitted for clarity.
Figure 9B:
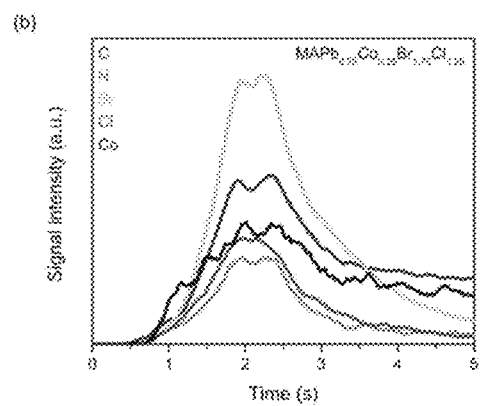
Figures 10A, 10B:
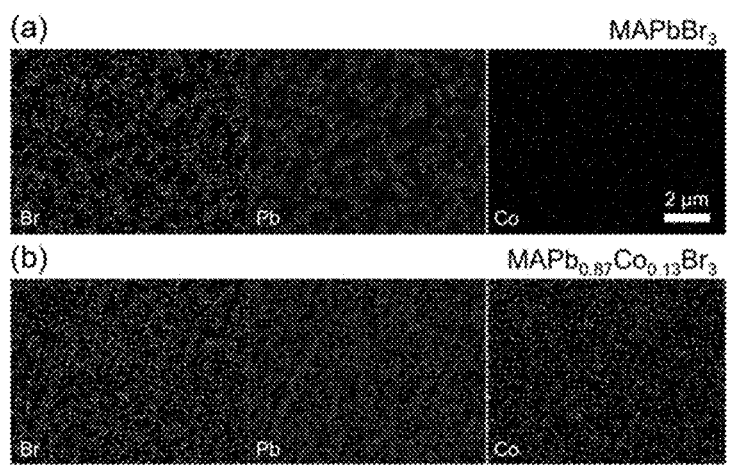
FIGS. 10A-B. EDX elemental mapping of FIGS. 9A $MAPbBr_3$ and 9B $MAPb_{0.87}Co_{0.13}Br_3$ thin films under the same data acquisition parameters. Green=Br, red=Pb, and blue=Co.

This prediction is born out in films of the mixed Br/Cl perovskite that appear more uniform by optical microscopy and SEM than Br-only perovskites; however, both Br-only and mixed halide films possess a homogeneous perovskite structure, as evidenced by X-ray diffraction (XRD) studies (vide infra). Additionally, all films displayed relatively uniform distributions of Fe2+/Co2+, Pb2+, and Br—/Cl—, both in the cross section of the films (see, FIGS. 7A,7B to FIGS. 8A, 8B) and across the planar direction of the films (see EDX maps, FIGS. 9A-9B). The relative ratios of the inorganic cations (Pb and Fe/Co) and the halides (Br and Cl) refer to the ratios of the precursors in solution prior to spin coating. It is likely that the final stoichiometry of each film is slightly different than this predicted values, but it is believed, for comparison to one another, these approximations are sufficient (generally=/−5%.

Structural Prediction and Characterization. It is believed that substitution occurs at or near the Pb sites, resulting in octahedral or distorted octahedral environments, and in turn perovskite or distorted perovskite-like structures. DFT calculations predict that ⅛ Co substitution for Pb in $MAPbBr_3$ and $MAPb(Br,Cl)_3$ will not change the lattice constant appreciably, as summarized in Table 1. Using PBE, the optimized lattice constant of MAPbBr3 is 6.062 Å with and insignificant change in lattice constant (Δlat=0.10%) to 6.066 Å upon Co substitution (MAPb0.87Co0.13Br3). The lattice constant is also largely insensitive to the U value selected. U of 3 and 7 eV result in lattice constants of 6.051 Å (Δlat=−0.17%) and 6.059 Å (Δlat=−0.04%), respectively. Similar behavior is also observed for the optimized lattice constant of $MAPbBr_{1.5}Cl_{1.5}$ alloy, which has smaller lattice constant than $MAPbBr_3$. In all calculations, the change of the lattice constant is less than or equal to 0.3%, consistent with experimental findings below.

TABLE 1

The optimized lattice constant of $MAPb_{1-x}M_xBr_{3-y}Cl_y$ (M = Co, Fe) from DFT calculations.

| Material | U for M 3d (eV) | Lattice constant (Å) | Change in lattice constant $\Delta_{lat}$ (%) |
|---|---|---|---|
| $MAPbBr_3$ | N/A | 6.065 | |
| $MAPb_{0.87}Co_{0.13}Br_3$ | 0 | 6.062 | −0.05 |
| | 3 | 6.057 | −0.13 |
| | 7 | 6.059 | −0.10 |
| $MAPb_{0.87}Fe_{0.13}Br_3$ | 0 | 6.057 | −0.13 |
| $MAPbBr_{1.5}Cl_{1.5}$ | N/A | 5.933 | |
| $MAPb_{0.87}Co_{0.13}Br_{1.5}Cl_{1.5}$ | 0 | 5.916 | −0.29 |
| | 3 | 5.922 | −0.19 |
| | 7 | 5.915 | −0.30 |

Figure 2A:
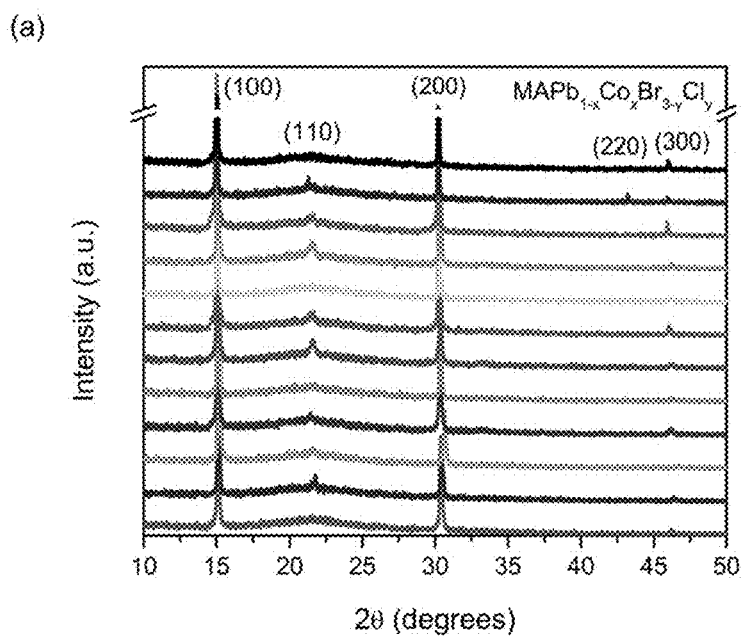
FIGS. 2A-D. (a) XRD patterns of $MAPb_{1-x}Co_xBr_{3-y}Cl_y$ films. (b) Zoomed in region of the (200) XRD peak. (c) Reflection angle of the (200) XRD peak as a function of y (% Cl) across all Co substitution levels. (d) Intensity and FWHM of (200) XRD peak with increasing y (% Cl). The lines are best linear fits to the data.
Figure 2B:
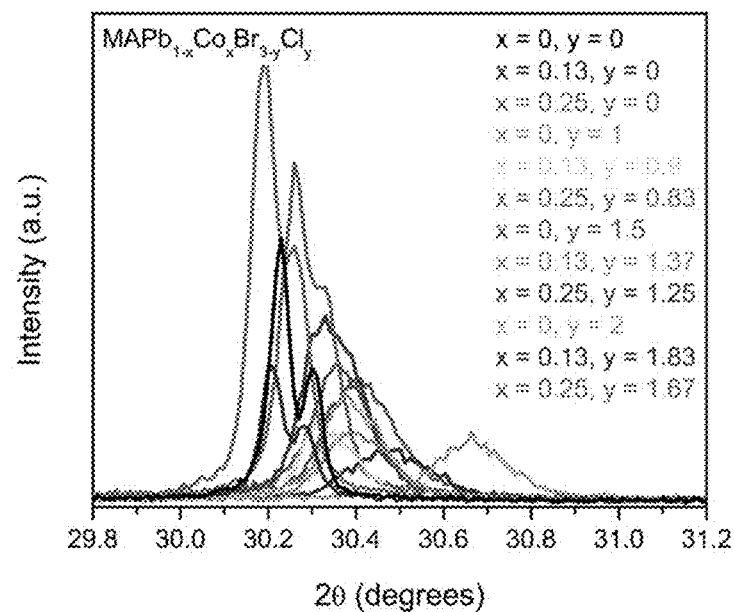
Figure 11:
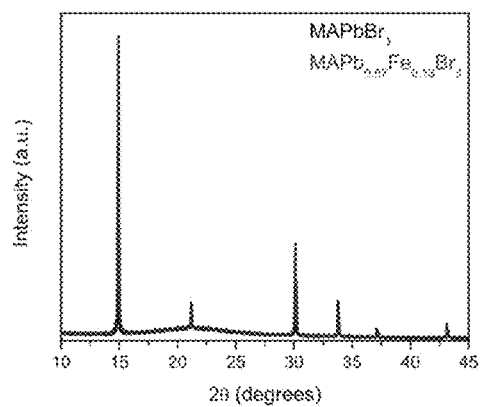
FIG. 11. XRD patterns of $MAPbBr_3$ (black) and Fe-substituted $MAPb_{0.87}Fe_{0.25}Br_3$ (red) thin films.
Figure 12:
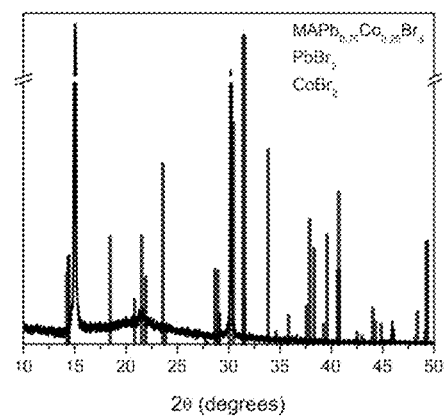
FIG. 12. Predicted XRD patterns for $PbBr_2$ (red) and $CoBr_2$ (blue), with the XRD pattern for a $MAPb_{0.75}Co_{0.25}Br_3$ (black) thin film shown for comparison.
Figure 13:
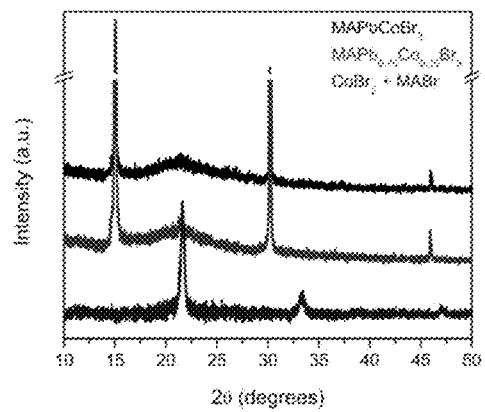
FIG. 13. XRD pattern of a control film consisting of a 1:1 ratio of $CoBr_2$ to MABr (blue), with XRD patterns for $MAPbBr_3$ (black) and $MAPb_{0.75}Co_{0.25}Br_3$ (red) thin films shown for comparison.

All levels of Fe and Co substitution studied (x=0.13 to 0.25 for Fe and x=0.13 to 0.5 for Co) result in films that exhibit the anticipated perovskite structure, as evidence by XRD patterns in FIG. 2A and FIG. 11. From the observed reflections, it is evident that each film formed the same Pm3m cubic crystal structure characteristic of $MAPbBr_3$ (FIG. 2a and FIG. 11). There is no indication of free $PbBr_2/PbCl_2$ or $FeBr_2/CoBr_2$ for substitution levels from x=0.13 to 0.5 (FIG. 12). Crystallinity of the films decreases considerably at substitution levels above x=0.25, and thus, for simplicity only levels of Co substitution of x=0.13 and 0.25 are included in these studies. For a control, a film was prepared consisting of a 1:1 ratio of $CoBr_2$ and MABr (i.e. substitution level of x=1), and this film no longer possesses the perovskite structure of $MAPbBr_3$ (FIG. 13). Fe substitution did not result in a sub-gap absorption feature (vide infra), and therefore, these films were not studied in further detail.

Figure 2C:
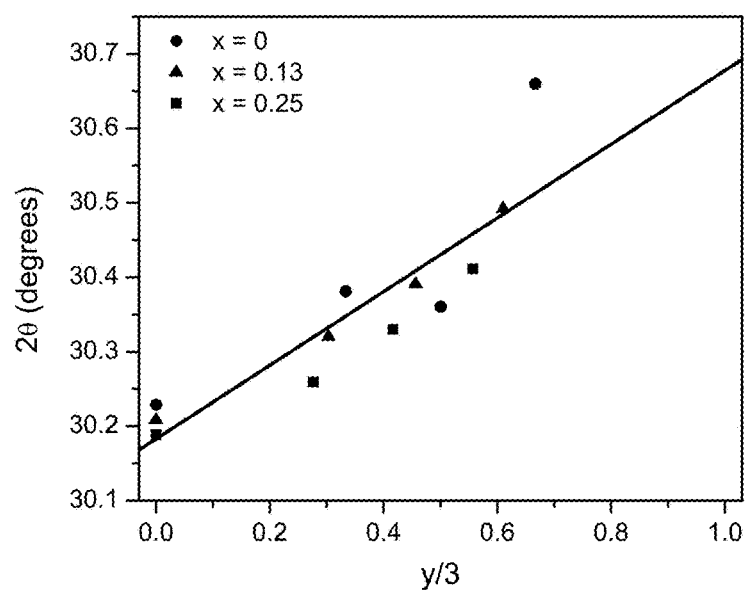
Figure 2D:
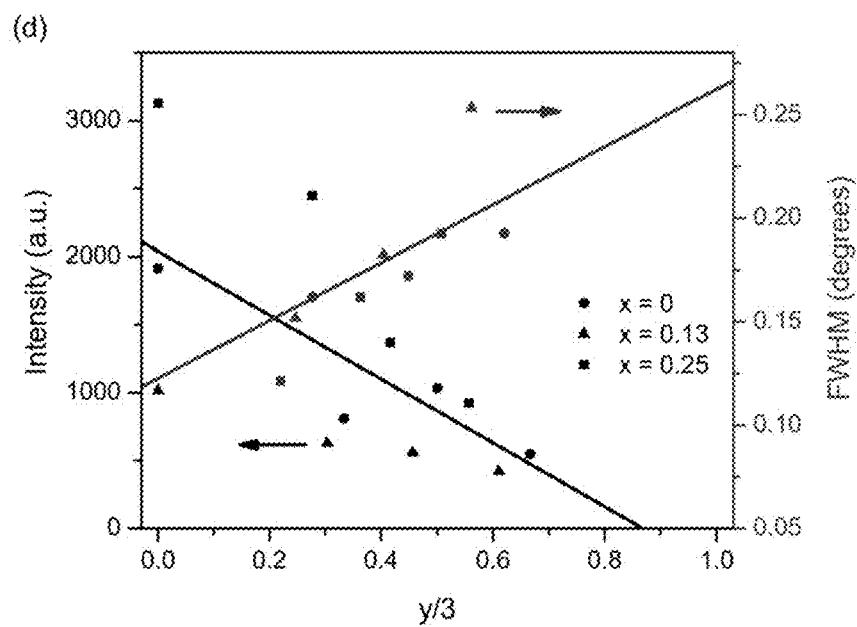

The lattice parameter and unit cell volume for the set of $MAPb_{1-x}Co_xBr_{3-y}Cl_y$ films varies from a=b=c=5.8836-5.8059 Å and V=203.67-195.71 Å³ (x=0, y=0 to x=0, y=3, respectively). As has been previously discussed, the unit cell dimensions of perovskite halides are primarily dictated by the composition of halides. This effect is also observed for our $MAPb_{1-x}Co_xBr_{3-y}Cl_y$ films, where 2θ increases with increasing y (% Cl), FIG. 2c. Consistent with calculations, incorporation of $Co^{2+}$ into the perovskite framework does not significantly change the dimensions of the unit cell. For mixed Sn/Pb perovskite halides, similar results were observed: the lattice parameter a changed from only 8.929 to 8.930 Å for $MAPbI_3$ and MASn0.25Pb0.7513, respectively, despite a large decrease in ionic radius (although less drastic, rSn=1.18 Å). For the Br-only perovskites, the lattice parameter and unit cell volume ranged from a=b=c=5.8836, 5.8876, 5.8876 Å and V=203.67, 204.09, 204.09 Å³ for Co concentrations of x=0, x=0.13, and x=0.25, respectively. Indeed, studies by the Applicant further support that the unit cell dimensions of perovskite halides, if the phase does form, are primarily dictated by the nature of the halides and are little affected by the nature of the organic/inorganic cations (A or B). Crystallinity, as estimated by peak intensity and FWHM, does, however, tend to decrease with increasing y (FIG. 2d). This effect is also unexpected, as it had been hypothesized that incorporating Cl— would form a more stable perovskite structure with Co2+, as determined by the tolerance and octahedral factors. One possible mechanism explaining this is that the smaller anion speeds up the crystallization process, resulting in smaller grain boundaries and less crystallinity.

First Principles Thermodynamics. The thermodynamics of Co substitution is investigated using DFT energies of $MAPbBr_3$ and $MAPb_{0.875}Co_{0.125}Br_3$. The formation energy for Co incorporation, calculated against binary bromide formation, is:

$$\Delta E = \frac{E(MA_8Pb_7MBr_{24}) + E(PbBr_2) - 8E(MAPbBr_3) - E(MBr_2)}{8} + k_BT\{x\ln x + (1-x)\ln(1-x)\}$$

where kB is the Boltzmann constant, x is ⅛, and T is growth temperature (100° C.). The values of ΔE, under different applied Hubbard U corrections for the Co d electrons, are 0.033 eV (U=0 eV), 0.030 eV (U=3 eV), and −0.099 eV (U=7 eV). These values are either similar or less than kBT at growth temperature (0.032 eV), or negative, indicating thermodynamic thermodynamic preference for Co incorporation into the MAPbBr$_3$ framework. Similar calculation was done to investigate the thermodynamics of Co substitution in MAPbBr$_{1.5}$Cl$_{1.5}$, and the calculated values of ΔE are 0.030 (U=0 eV), 0.031 (U=3 eV), and −0.109 eV (U=7 eV), quite similar to those in MAPbBr$_3$.

Characterization.

Samples were made in accordance with the above described methods. XRD measurements were performed with a Bruker D2 Phaser diffractometer with Cu Kα radiation. The scan range was between 10 and 50° with a 0.01° step size and a time per scan of 0.05 s. Glow discharge optical emission spectroscopy (GDOES) was performed with a Horiba GD-Profiler 2 spectrometer. Scanning electron microscopy (SEM) images were collected on a Hitachi S4700-II equipped with an energy dispersive X-ray (EDX) detector for elemental analysis. Optical absorption spectra were measured using a Varian Cary 5000 UV-Vis-NIR spectrophotometer equipped with an integrating sphere diffuse reflectance accessory. Absorption coefficients were calculated by correcting for the absorbance of the substrate, reflectance of the film, and the thickness of the film. Both steady state PL emission spectra and time-resolved PL, measured at the Center for Nanoscale Materials at Argonne National Laboratory, were obtained using a 405 nm, 35 ps pulse width diode laser operated at 1 MHz. PL signals were collected with a 75 mm focal length lens, passed through a 435 nm long pass filter, and directed onto a 0.3 m focal length spectrograph. Static PL spectra were collected with a cooled CCD, and time-resolved PL dynamics were recorded using an avalanche photodiode and time-correlated single photon counting electronics at specified emission wavelengths. Time constants for time-resolved PL were obtained by fitting PL decays to a biexponential function (y=A1*exp(x/τ1)+A2*exp(x/τ2)) in Origin.

Computational Studies. To investigate the optoelectronic property of MAPb$_{1-x}$Co$_x$Br$_3$, the calculations are performed within the density functional theory (DFT) framework by using the generalized gradient approximation (GGA) parameterized by Perdew, Burke and Ernzerhof for the exchange correlation potential, see Perdew, J. P.; Burke, K.; Ernzerhof, M. Generalized Gradient Approximation Made Simple. *Phys. Rev. Lett.* 1996, 77, 3865-3868. The projector-augmented wave (PAW) potentials were used, as implemented in the VASP code. (See, e.g., (40) Blöchl, P. E. Projector augmented-wave method. *Phys. Rev. B* 1994, 50, 17953-17979. Kresse, G.; Furthmüller, J. Efficient iterative schemes for ab initio total-energy calculations using a plane-wave basis set. *Phys. Rev. B* 1996, 54, 11169-11186.) The wavefunctions are expanded in plane waves with an energy cutoff of 500 eV. The atomic structures were fully relaxed until the residual forces were less than 0.035 eV/A. Substitutional calculations are performed using 2×2×2 supercells of MAPbBr$_3$, containing 96 atoms. Absorption coefficients are calculated from the frequency-dependent dielectric function, obtained from summation over empty states. For the relaxation and dielectric function calculations, 4×4×4 and 8×8×8 Monkhorst-Pack meshes were used for Brilluoin zone integration, respectively. Band unfolding has been performed using the BandUP code.

Generally speaking, the metal d bands are not accurately calculated in GGA calculations, and thus the effects of on-site Coulomb correlation, which is described by a Hubbard-like (U) term, is examined. The implementation of Dudarev for the Hubbard U correction is used, while the values of U for oxides have been calibrated to reproduce reaction energies derived from experimental enthalpies of formation, experimental data available for bromides/chlorides are insufficient for this purpose. However, the appropriate value of U for Co oxides to reproduce reaction energies have been found to be 3.3-3.5 eV, and one expect the appropriate U values for chlorides and bromides to be lower than those for oxides. Calculations of Co fluorides, CoF$_2$ and CoF$_3$, also show that U value which reproduces the reaction energy is in the range of 0.3-2 eV, indicating that U value for Co is not large. On the other hand, using U=7 eV reproduces the absorption properties of CoBr$_2$, and in general the U values required to reproduce electronic structure properties at the single-particle level tend to be higher than those required to reproduce reaction energies. Therefore, the DFT+U calculations were performed with U=0, 3, and 7 eV.

Figure 3A:
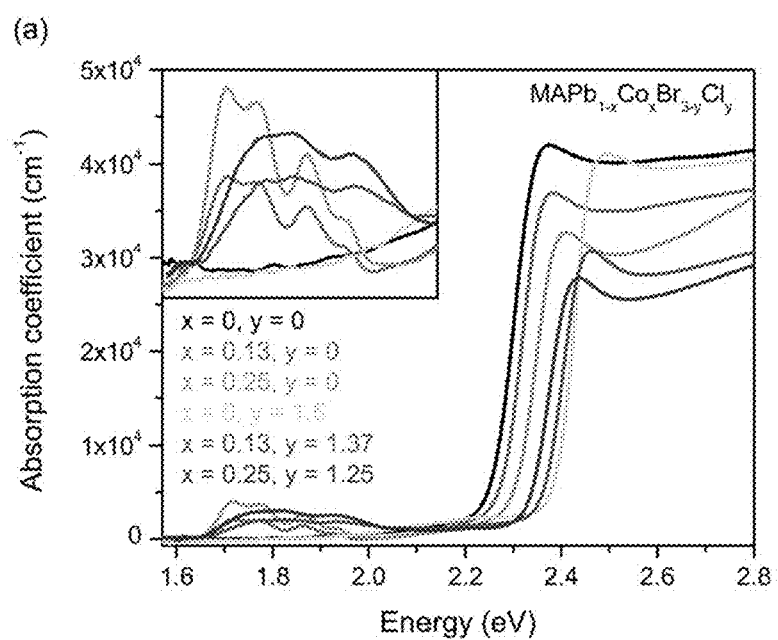
FIGS. 3A-B. (a) Absorption spectra and (b) normalized PL spectra of $MAPb_{1-x}Co_xBr_{3-y}Cl_y$ thin films.
Figure 14:
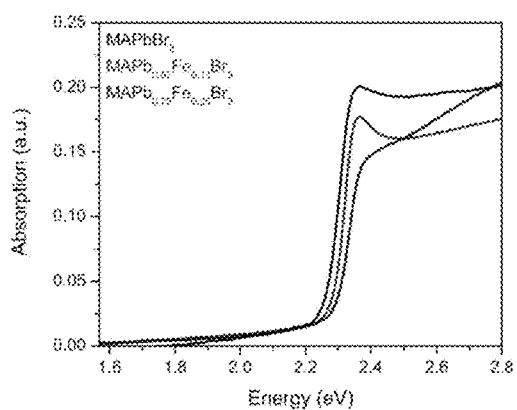
FIG. 14. Absorption spectra of $MAPbBr_3$ (black), $MAPb_{0.87}Fe_{0.13}Br_3$ (red), and $MAPb_{0.75}Fe_{0.25}Br_3$ (blue) thin films, showing no mid-band gap absorption.
Figure 15:
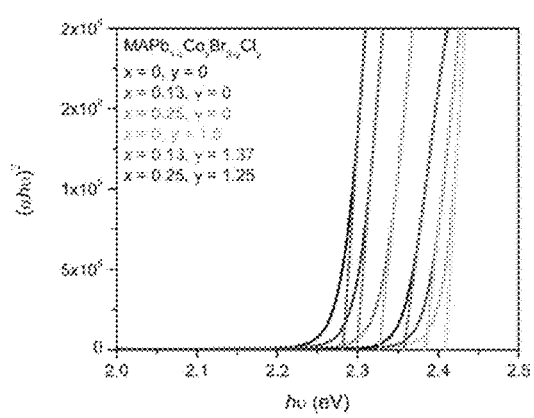
FIG. 15. Tauc plots of the band gap for $MAPb_{1-x}Co_xBr_{3-y}Cl_y$ thin films on FQ.
Figure 16:
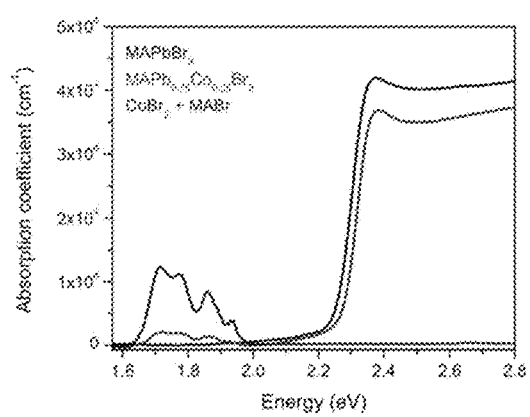
FIG. 16. Absorption spectrum of a control film consisting of a 1:1 ratio of $CoBr_2$ to MABr (blue), with the absorption spectra for $MAPbBr_3$ (black) and $MAPb_{0.75}Co_{0.25}Br_3$ (red) thin films shown for comparison.
Figure 17:
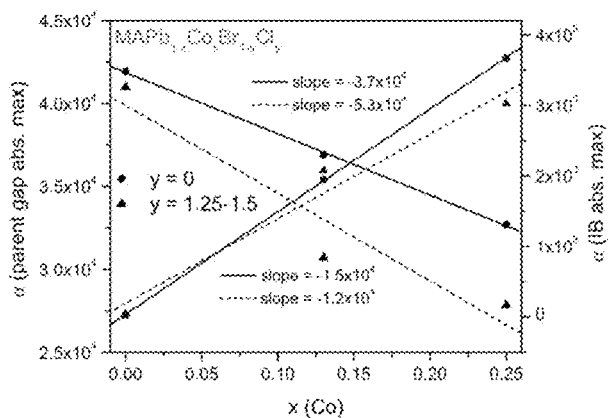
FIG. 17. Peak absorption coefficient (a) for the parent gap (left axis) and Co-based mid-gap states (right axis) as a function of the amount of Co in the substituted film (x) for $MAPb_{1-x}CoBr_{1-y}Cl_y$. Linear fits of the data are shown to indicate trends.
Figure 18:
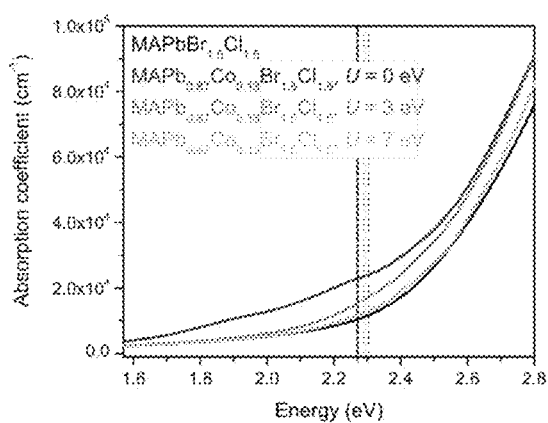
FIG. 18. Calculated absorption coefficient of $MAPb_{0.87}Co_{0.13}Br_{1.5}Cl_{1.5}$ with U values (for Co 3d orbitals) of 0 (red), 3 (orange), and 7 eV (yellow) as compared to the calculated absorption coefficient of $MAPbBr_{1.5}Cl_{1.5}$ (black). The calculated band gaps are indicated with vertical dotted lines.
Figures 19A, 19B:
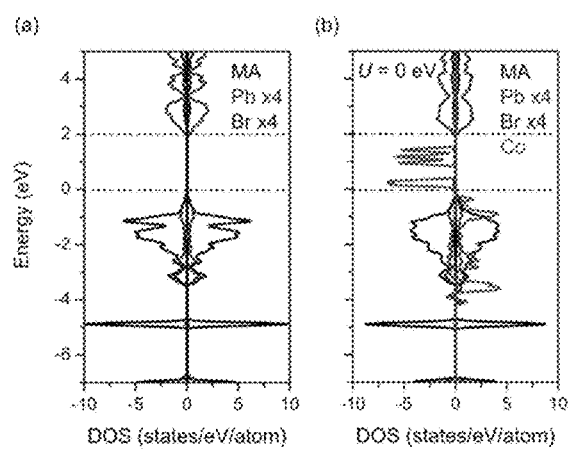
FIGS. 19A-B. Calculated electronic structure of (a) $MAPbBr_3$ and (b) $MAPb_{0.87}Co_{0.13}Br_3$ with a Hubbard U=0 eV used for Co d orbitals. The dashed horizontal lines represent the band edges of pure $MAPbBr_3$ estimated by N core level as reference in the calculations.
Figures 20A, 20B:
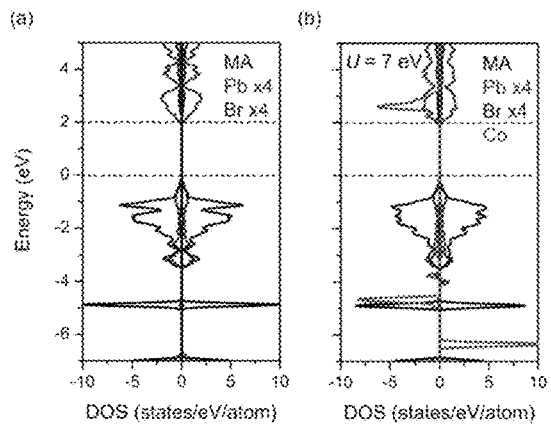
FIGS. 20A-B. Calculated electronic structure of (a) $MAPbBr_3$ and (b) $MAPb_{0.87}Co_{0.13}Br_3$ with a Hubbard U=7 eV used for Co d orbitals. The dashed horizontal lines represent the band edges of pure $MAPbBr_3$ estimated by N core level as reference in the calculations.
Figure 21:
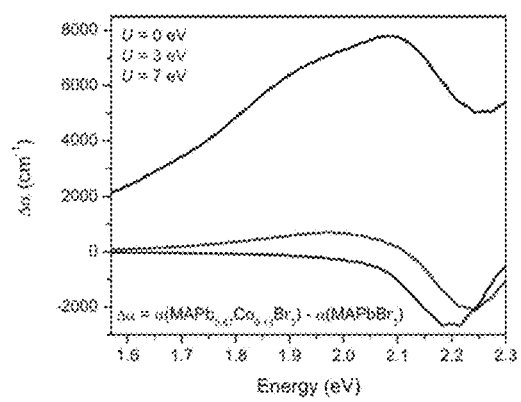
FIG. 21. Change in absorption coefficient ($\Delta\alpha$) of $MAPb_{0.87}Co_{0.13}Br_3$ from $MAPbBr_3$ for U values (for Co 3d orbitals) of 0 (black), 3 (red), and 7 eV (blue).
Figure 22:
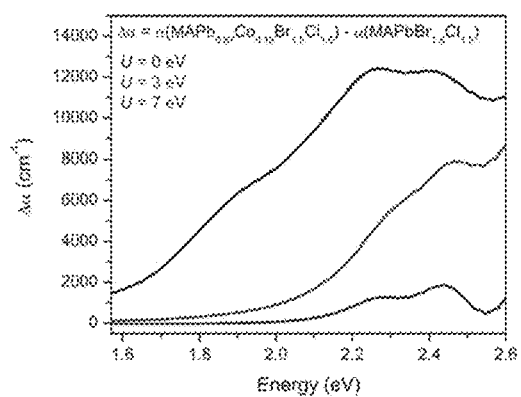
FIG. 22. Change in absorption coefficient ($\Delta\alpha$) of $MAPb_{0.87}Co_{0.13}Br_{1.5}Cl_{1.5}$ from $MAPbBr_{1.5}Cl_{15}$ for U values (for Co 3d orbitals) of 0 (black), 3 (red), and 7 eV (blue).
Figures 23A, 23B:
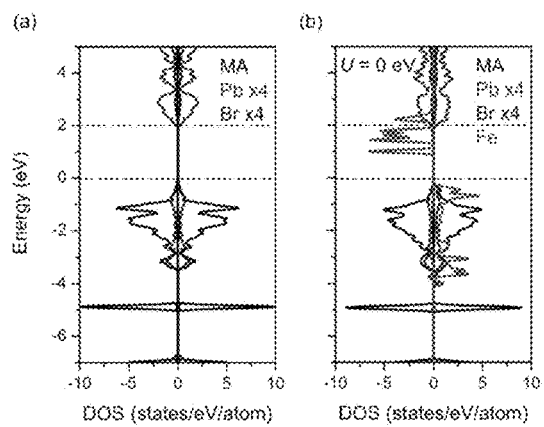
FIGS. 23A-B. Calculated electronic structure of (a) $MAPbBr_3$ and (b) $MAPb_{0.87}Fe_{0.13}Br_3$ with a Hubbard U=0 eV used for Fe d orbitals. The dashed horizontal lines represent the band edges of pure $MAPbBr_3$ estimated by N core level as reference in the calculations.
Figure 24:
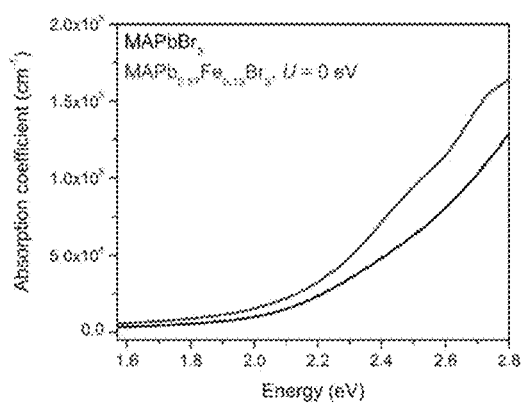
FIG. 24. Calculated absorption coefficient of $MAPb_{0.87}Fe_{0.13}Br_3$ with a Hubbard U=0 eV used for Fe d orbitals (red) as compared to the calculated absorption coefficient of $MAPbBr_3$ (black).
Figure 25:
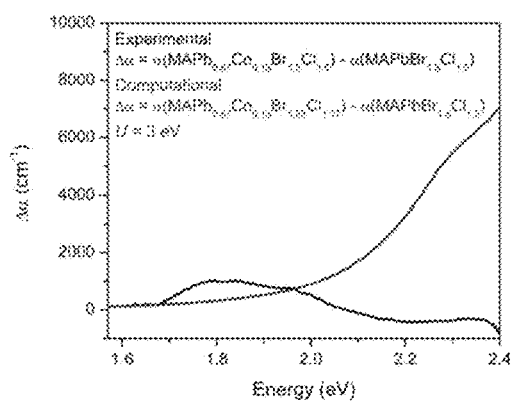
FIG. 25. Change in absorption coefficient ($\Delta\alpha$) of $MAPb_{0.87}Co_{0.13}Br_{1.55}Cl_{1.5}$ from $MAPbBr_{1.5}Cl_{1.5}$ for experimental (black) and computations (red, U=3 eV). The experimental difference plot has a Br and Cl content of $Br_{1.63}Cl_{1.37}$.

Electronic Structure and Optical Properties. Reflectance-corrected, steady state absorption spectra were obtained for the Fe- and Co-substituted MAPb$_{1-x}$Fe$_x$Br$_{3-y}$Cl$_y$ and MAPb$_{1-x}$Co$_x$Br$_{3-y}$Cl$_y$ films (FIGS. 14 and 3a). Fe substitution did not result in a sub-gap absorption feature (see FIG. 14), and therefore, these films were not further examined. For each Co-substituted film, the absorption spectrum shows a sharp band edge and exciton peak that is characteristic of MAPbBr$_3$ thin films. Band gaps extracted from Tauc plots display values of 2.27, 2.29, and 2.31 eV for MAPb$_{1-x}$Co$_x$Br$_3$ (x=0, 0.13, 0.25, respectively; see FIG. 15). The band gaps of the other MAPb$_{1-x}$Co$_x$Br1-yCl$_y$ films corresponding to the absorption spectra shown in FIG. 3a are listed in Table 2. In addition to the band edge, Co-substituted samples display an additional sub-band gap absorption feature between 1.65-2.0 eV. This feature is made up of at least four closely spaced peaks and becomes broader with a shift to slightly higher energy in the Cl-containing films. The multiplet centered at ~1.8 eV is characteristic of CoBr2 in a Br-rich environment, commonly represented as either [CoBr$_4$]$_2$- or [CoBr$_6$]$_4$—. For comparison, this feature is also present in a control sample of CoBr$_2$ and MABr (no Pb, x=1; see FIG. 16). Both the observation of a shift of this Co-related absorption in the Cl-containing films and the shift in band gap of the MAPbBr$_{1.5}$Cl$_{1.5}$ film upon adding CoBr$_2$, provide further evidence that Co is chemically incorporated into perovskite structure. No evidence was observed for segregated states, such as Br- or Cl-phase separation, by the absorption spectra. An intermediate band energy level diagram consistent with these absorption spectra is shown in FIGS. 5A-C.

Figure 6B:
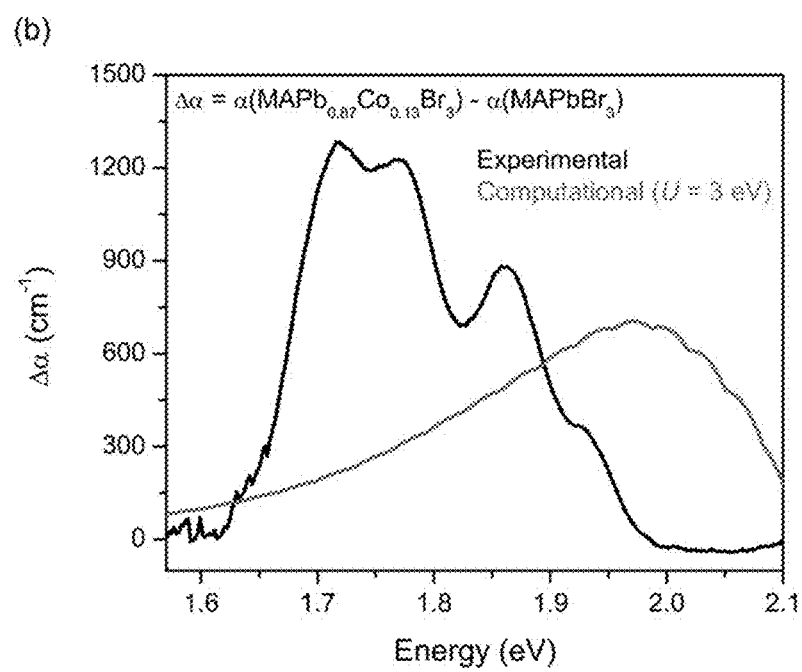
Figure 7:
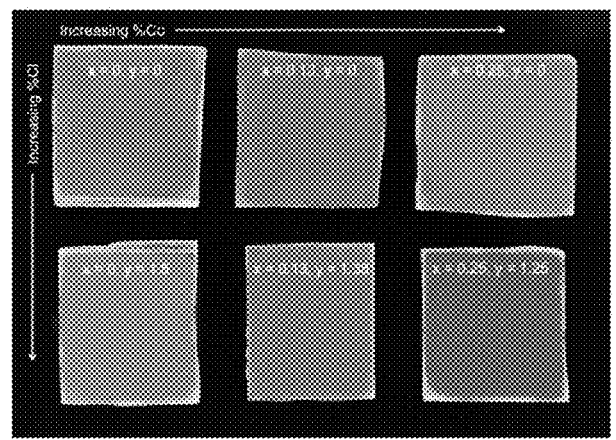
FIG. 7. Photograph of $MAPb_{1-x}Co_xBr_{3-y}Cl_y$ thin films on FQ
Figure 8A:
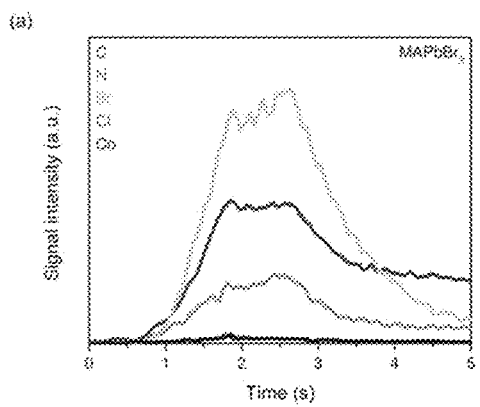
FIGS. 8A-B. Glow discharge optical emission spectroscopy (GDOES) of FIG. 8A $MAPbBr_3$ and FIG. 8B $MAPb_{0.75}Co_{0.25}Br_3$ thin films. The signals for oxygen and hydrogen have been omitted for clarity.
Figure 8B:
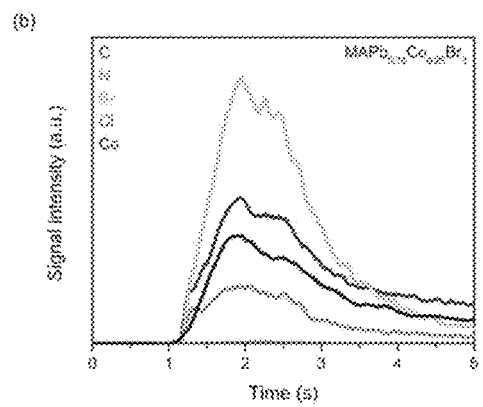

The computationally predicted electronic densities of states, band structure, and absorption coefficient for MAPbBr$_3$, MAPb$_{0.875}$Co$_{0.125}$Br$_3$, MAPbBr$_{1.5}$Cl$_{1.5}$, and MAPb$_{0.875}$Co$_{0.125}$Br$_{1.5}$Cl$_{1.5}$ are in reasonable agreement with experiment (see FIGS. 5A-C). DFT and DFT+U approaches both predict mid-gap states induced by Co substitution, regardless of the value of U (from 0 to 7 eV). The positions of the mid-gap states and the intensity of sub-gap absorption vary slightly with the value of U. In the DFT (PBE) calculation of MAPb$_{0.875}$Co$_{0.125}$Br$_3$, there are three empty intermediate bands and the two occupied levels in the band gap for spin up whereas there is no gap state for spin down (not shown). Because of the intermediate bands, the absorption at relatively low energy is enhanced as compared to pure MAPbBr$_3$ and MAPbBr$_{1.5}$Cl$_{1.5}$. In the DFT+U calculations, on-site Coulomb potential increases (decreases) the position of the unoccupied (occupied) gap states. As a result, the occupied levels are all below the valence band maximum with U=3 eV, however, three unoccupied levels are still remained in the band gap, as shown in FIG. 5. The intermediate bands are mainly composed of Co d orbitals, and small amount of Br p orbital characters are mixed. As the unoccupied levels are increased in energy, photon transition energy is also increased, which is reflected in the absorption, FIG. 6. The absorption calculated within DFT shows absorption at lower energy than the band gap energy, but this extra absorption by Co incorporation is shifted to higher energy, and becomes less distinguishable from the absorption of host materials. When relatively strong Coulomb potential of U=7 eV is applied, the unoccupied levels becomes even higher than the conduction band minimum, showing no extra gain in absorption at the lower energy, in contrast to the experiments. This indicates that U of 7 eV is too strong to model Co alloyed hybrid perovskites; therefore, calculations without U (U=0 eV) and with U of 3 eV can be regarded as bounds. In addition, the calculated band gap of MAPbBr3 and MAPbBr1.5Cl1.5 are 1.97 and 2.27 eV, respectively. As the band gap is increased by 0.3 eV, the absorption spectra are also shifted to higher energy. Preferably, the intermediate bands are partially occupied.

In addition, Co substitution increases the energy of the main absorption edge by ~0.2 eV, again irrespective of the value of U.

Figure 3B:
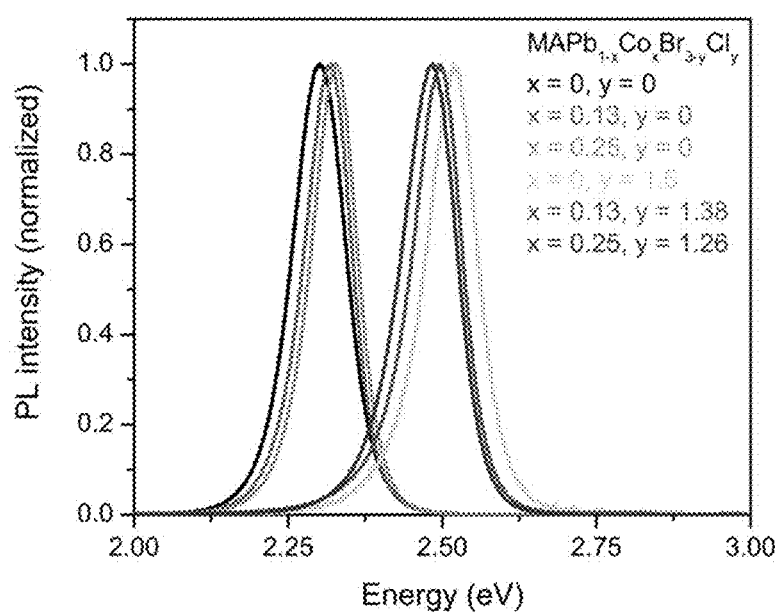

All of the Br-only perovskite films display intense steady state photoluminescence ("PL"), which shifts to slightly higher energy upon substitution with Co (FIGS. 3b and 26). The PL peak is centered at 2.30, 2.32, and 2.33 eV for $MAPb_{1-x}Co_xBr_3$ x=0, 0.13, and 0.25, respectively (FIG. 3b and Table 2). The increase in bandgap is consistent with prediction, although of a smaller magnitude. The difference is considered to be within the margin of uncertainty for bandgap computed from DFT. These intense steady state PL measurements suggest that the long excited state lifetimes that allow for radiative relaxation in the parent material are largely preserved in the new alloy. (see table 3) Cl-incorporation significantly diminishes PL intensity. There are contradictory studies in the literature on the effect of Cl-incorporation on photoluminescence properties. Yan et al. conclude that Cl-incorporation decreases PL intensity (as Applicant observed), but can enhance PL intensity in a high MABr concentration environment. Zhang et al. conclude that Cl-incorporation increases PL intensity; however, the significant enhancements are only observed for relatively low Cl stoichiometry (y<1.2). The PL peaks for mixed Br/Cl perovskite films are shifted to higher energy, consistent with the shift in band gap. The PL peak is centered at 2.52, 2.50, and 2.48 eV for $MAPbBr_{1.5}Cl_{1.5}$, $MAPb_{0.87}Co_{0.13}Br_{1.63}Cl_{1.37}$, and $MAPb_{0.75}Co_{0.25}Br_{1.75}Cl_{1.25}$, respectively (FIG. 3b and Table 2 below). For each set of films shown in FIG. 3b, substitution of Co for Pb in the perovskite framework results in increased PL intensity over the parent material (FIG. 26). Additionally, no PL features were observed for any films in the range of 1.6-2.0 eV, where one would expect to observe features from the Co-related IB. This suggests that, in its current state, the IB is inaccessible via relaxation from parent perovskite PL. That is, in its current state, cobalt is producing a mid-gap state that is in the right position to be an IB band. But, because it is inaccessible via relaxation from parent perovskite PL, it doesn't satisfy all of the requirements of an IB material. By tuning the electron density of this mid-gap state, this could be achieved. No PL was observed for the films upon excitation with 1.6-1.9 eV light (energy equivalent to the Co-related IB, see FIG. 3a).

TABLE 2

Band gaps extracted from Tauc plots and PL peaks.

| $MAPb_{1-x}Co_xBr_{1-y}Cl_y$ | Band Gap (eV) | PL peak (eV) |
|---|---|---|
| x = 0, y = 0 | 2.27 | 2.30 |
| x = 0.13, y = 0 | 2.29 | 2.32 |
| x = 0.25, y = 0 | 2.31 | 2.33 |
| x = 0, y = 1.5 | 2.40 | 2.52 |
| x = 0.13, y = 1.37 | 2.37 | 2.50 |
| x = 0.25, y = 1.25 | 2.35 | 2.48 |

Figure 4A:
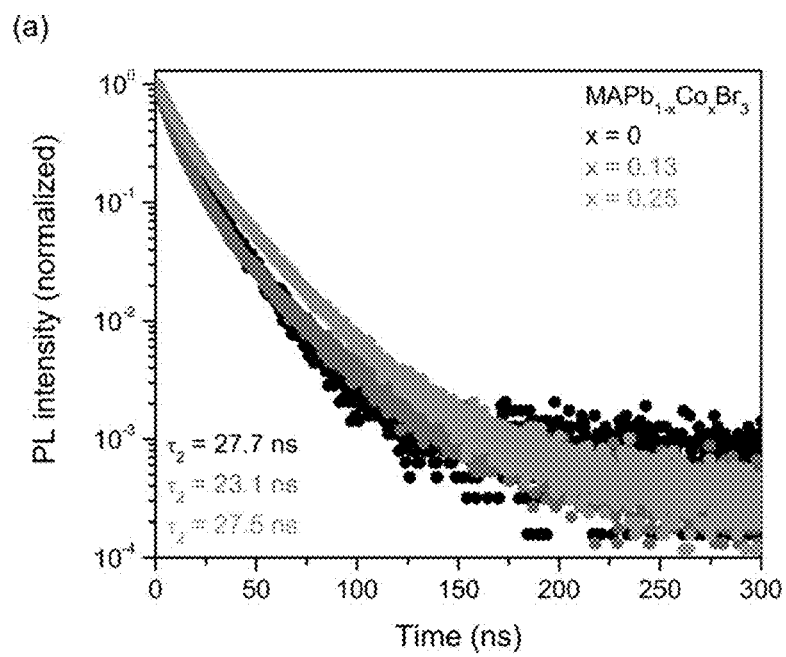
FIGS. 4A-B. Time-resolved PL of (a) Br-only (y=0) films revealing dependence on x, and (b) the halogen dependence on equally Co-substituted (x=0.25) films revealing a significant dependence on the Br/Cl ratio.
Figure 4B:
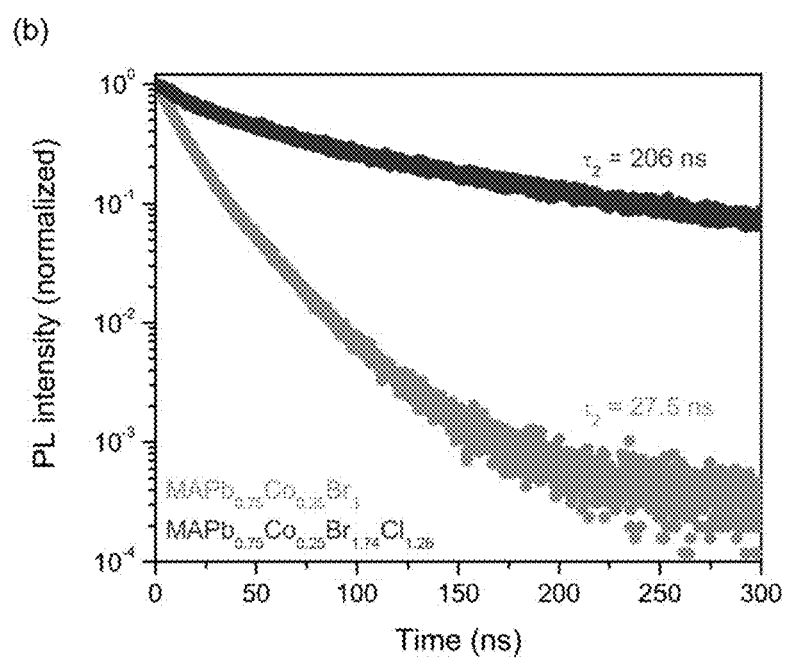

To determine the effect that Co substitution has on photoexcited carrier lifetimes, time-resolved PL data (FIGS. 4A-B) was obtained. For each film studied, the PL intensity displays a decay that was sufficiently modeled by a two-component exponential (FIGS. 27A-B). For the Br-only containing perovskites, the first component possesses a lifetime of $\tau 1$=~10 ns, and the second component possesses a lifetime of $\tau 2$=~26 ns. Substitution with Co did not have a significant effect on either of these lifetimes for the Br-only films (FIG. 4a). For applications in IB PVs, it's important to retain the long-lived photoexcited state lifetimes of perovskite films, and therefore, this result shows promise for creating quality IB materials from the Co-substituted films. Mixed Br/Cl perovskites containing Co possess nearly a magnitude higher PL lifetime than Br-only films with an equivalent about of Co ($\tau 2$=27.5 and 206 ns for $MAPb_{0.75}Co_{0.25}Br_3$ and $MAPb_{0.75}Co_{0.25}Br_{1.75}Cl_{1.25}$, respectively, FIG. 4b). Large-grain $MAPbBr_3$ films typically display lifetimes on the order of 100-200 ns; however, there is disputed in the art with regard to this and Applicant has observed lifetimes for $MAPbBr_3$ lower than many reports of high-quality films. Regardless, the lifetimes observed by Applicant are sufficient for direct comparison with Co-substituted samples. For certain embodiments of mixed Br/Cl perovskite films, lifetimes are observed in much better agreement with literature values for high-quality mixed halide films. The increase in lifetime with Cl-incorporation in our films is also consistent with previous reports. (See Table 3)

TABLE 3

Lifetimes extracted from exponential fits of time-resolved PL data.

| $MAPb_{1-x}Co_xBr_{1-y}Cl_y$ | $\tau_1$ (ns) | $\tau_2$ (ns) |
|---|---|---|
| x = 0, y = 0 | 11.0 | 27.7 |
| x = 0.13, y = 0 | 7.46 | 23.1 |
| x = 0.25, y = 0 | 11.2 | 27.5 |
| x = 0.25, y = 1.25 | 39.8 | 206 |

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A substituted perovskite comprising:
a material having the formula:

$$APb_{1-x}B_xBr_{3-y}Cl_y,$$

where A is a cation, B is Fe or Co, X is greater than 0 and less than 1 and y is 0-3).

2. The substituted perovskite of claim 1, wherein the cation is selected from the group consisting of methyl ammonium, formamidinium, and cesium.

3. The substituted perovskite of claim 1, having a tolerance factor of 0.813-1.107.

4. The substituted perovskite of claim 1, wherein y=0.

5. The substituted perovskite of claim 1 wherein y is greater than zero.

6. The substituted perovskite of claim 1 wherein x is 0.5 or less.

7. The substituted perovskite of claim 1, wherein B is Fe.

8. The substituted perovskite of claim 1, wherein B is Co.

9. A substituted perovskite comprising:
a material having the formula:

$$MAPb_{1-x}B_xBr_{3-y}H_y,$$

where MA is methyl ammonium, B is Fe or Co, H is a halide, X is 0 to 0.5 and y is greater than 0 and less than 3.

10. The substituted perovskite of claim 9, wherein y=1.5.

11. The substituted perovskite of claim 9, wherein B is Fe.

12. The substituted perovskite of claim 9, wherein B is Co.

13. The substituted perovskite of claim 9, having a tolerance factor of 0.813-1.107.

14. The substituted perovskite of claim 9, wherein H is Cl.

15. An article of manufacture comprising:
a glass substrate; and
a material deposited on the glass substrate having the formula:

$$APb_{1-x}B_xBr_{3-y}Cl_y,$$

where A is a cation, B is Fe or Co, X is 0 to 1 and y is 0 to 3.

16. The article of manufacture of claim 15 comprising wherein the cation is selected from the group consisting of methyl ammonium, formamidinium, and cesium.

17. The article of manufacture of claim 15 where y=0.

18. The article of manufacture of claim 15 wherein x=0.

19. The article of manufacture of claim 15 wherein y is greater than 0.

20. The article of manufacture of claim 15 wherein x is greater than 0.

* * * * *